(12) United States Patent
Maines

(10) Patent No.: US 6,969,610 B2
(45) Date of Patent: Nov. 29, 2005

(54) METHODS OF MODIFYING CELL STRUCTURE AND REMODELING TISSUE

(75) Inventor: Mahin D. Maines, Rochester, NY (US)

(73) Assignee: University of Rochester, Rochester, NY (US)

(*) Notice: Subject to any disclaimer, the term of this patent is extended or adjusted under 35 U.S.C. 154(b) by 30 days.

(21) Appl. No.: 10/045,545

(22) Filed: Jan. 14, 2002

(65) Prior Publication Data

US 2003/0027124 A1 Feb. 6, 2003

Related U.S. Application Data

(60) Provisional application No. 60/261,500, filed on Jan. 12, 2001.

(51) Int. Cl.[7] .................... C12N 15/63; C12N 9/16; C12N 15/86; C12N 7/01; C12N 5/16; C12N 5/22; C07H 21/04

(52) U.S. Cl. .................. 435/455; 435/196; 435/456; 435/235.1; 435/325; 435/366; 435/368; 435/371; 435/372; 435/377; 536/23.2

(58) Field of Search .................... 435/455, 196, 435/456, 235.1, 325, 366, 368, 371, 372, 377, 189, 375; 536/23.2

(56) References Cited

PUBLICATIONS

Salim et al Human biliverdin reductase is autophosphorylated, and phosphorylation is required for bilirubin formation. J Biol Chem. Apr. 6, 2001;276(14): 10929–34. Epub Jan. 17, 2001.*
Baranano et al, Biliverdin reductase: a major physiologic cytoprotectant. Proc Natl Acad Sci U S A. Dec. 10, 2002;99(25):16093–8. Epub Nov. 27, 2002.*
Leipe et al Bilirubin–induced cytomorphological changes in guinea–pig leucocytes. Biomed Biochim Acta. 1983;42(5):503–10.*
Argiro V, Bunge MB, Johnson MI. A quantitative study of growth cone filopodial extension. J Neurosci Res 1985;13(1–2):149–62.*
Ausubel et al. Expression of proteins in mammalian cells. Unit 16.12. In: Current Protocols in Molecular Biology 1997 Wiley Press.*
Panahian et al., "Enhanced Neuronal Expression of the Oxidoreductase—Biliverdin Reductase—After Permanent Focal Cerebral Ischemia," *Brain Research* 850:1–13 (1999).
Maines et al., "Spin Trap (N–t–butyl–α–phenylnitrone)–Mediated Suprainduction of Heme Oxygenase–1 in Kidney Ischemia/ Reperfusion Model: Role of the Oxygenase in Protection Against Oxidative Injury," *The Journal of Pharmacology and Experimental Therapeutics* 291(2):911–919 (1999).

Maines et al., "Human Biliverdin IXα Reductase is a Zinc–Metalloprotein: Characterization of Purified and *Escherichia coli* Expressed Enzymes," *Eur. J. Biochem.* 235:372–381 (1996).
McCoubrey et al., "Site–Directed Mutagenesis of Cysteine Residues in Biliverdin Reductase: Roles in Substrate and Cofactor Binding," *Eur. J. Biochem.* 22:597–603 (1994).
Ewing et al., "Biliverdin Reductase is Heat Resistant and Coexpressed with Constitutive and Heat Shock Forms of Heme Oxygenase in Brain," *J. Neurochem.* 61:1015–1023 (1993).
Maines et al., "Purification and Characterization of Human Biliverdine Reductase," *Archives of Biochemistry and Biophysics* 300(1):320–326 (1993).
Fakhrai et al., "Expression and Characterization of a cDNA for Rat Kidney Biliverdin Reductase," *J. Biol. Chem.* 267(6):4023–4029 (1992).
Huang et al., "Detection of 10 Variants of Biliverdin Reductase in Rat Liver by Two–Dimensional Gel Electrophoresis," *J. Biol. Chem.* 264(14):7844–7849 (1989).
Huang et al., "Microheterogeneity of Biliverdin Reductase in Rat Liver and Spleen: Selective Suppression of Enzyme Variants in Liver by Bromobenzene," *Archives of Biochemistry and Biophysics* 274(2):617–625 (1989).
Huang et al., "Multiple Forms of Biliverdin Reductase: Modification of the Pattern of Expression in Rat Liver by Bromobenzene," *Archives of Biochemistry and Biophysics* 270(2):513–520 (1989).
Kutty et al., "Biliverdin Reductase: Characterization in the Rat Kidney and the Inhibition of Activity by Mercuric Chloride," *Biochem. Pharmac.*32(13):2095–2102 (1983).
Kutty et al., "Purification and Characterization of Biliverden Reductase from Rat Liver," *J. Biol. Chem.* 256(8):3956–3962 (1981).

(Continued)

*Primary Examiner*—Rebecca E. Prouty
*Assistant Examiner*—Sheridan Swope
(74) *Attorney, Agent, or Firm*—Nixon Peabody LLP

(57) ABSTRACT

Disclosed is a method of modifying cell structure which includes: increasing the intracellular concentration of biliverdin reductase, or a fragment or variant thereof, in a mammalian cell under conditions effective to modify the structure of the mammalian cell. Also disclosed are methods of performing in vivo tissue remodeling in a mammal and repairing a damaged organ or organ system. Both of these methods include delivering biliverdin reductase, or fragments or variants thereof, to one or more cells present at a site of tissue remodeling in a mammal, wherein said delivering increases the intracellular concentration of biliverdin reductase, or fragments or variants thereof, under conditions effective to modify the structure of the one or more cells at the site of tissue remodeling, thereby remodeling the tissue containing the one or more cells.

5 Claims, 6 Drawing Sheets

PUBLICATIONS

Kutty et al., "Oxidation of Heme c Derivatives by Purified Heme Oxygenase," *J. Biol. Chem.* 257(17):9944–9952 (1982).

Van Bergen, "Hemoglobin and Iron–Evoked Oxidative Stress in the Brain: Protection by Bile Pigments, Manganese and S–Nitrosoglutathione," *Free Rad. Res.* 31:631–640 (1999).

Qato et al., "Prevention of Neonatal Hyperbilirubinaemia in Non–Human Primates by Zn–Protoporphyrin," *Biochem. J.* 226:51–57 (1985).

Magnusson et al., "Heme Oxygenase–1, Heme Oxygenase–2 and Biliverdin Reductase in Peripheral Ganglia from Rat, Expression and Plasticity," *Neuroscience* 95(3):821–829 (2000).

Ewing et al., "Immunohistochemical Localization of Biliverdin Reductase in Rat Brain: Age Related Expression of Protein and Transcript," *Brain Research* 672:29–41 (1995).

Frydman et al., "Identification of the Amino Acid Residues Essential for the Activity and the Interconversion of the Molecular Forms of Biliverdin Reductase," *Biochimica et Biophysica Acta* 1040:119–129 (1990).

McCoubrey et al., "The Structure, Organization and Differential Expression of the Rat Gene Encoding Biliverdin Reductase," *Gene* 160:235–240 (1995).

Huang et al., "Bromobenzene–Mediated Alteration in Activity and Electrophoretic Pattern of Biliverdin Reductase Variants in Rat Kidney," *Mol. Pharmacol.* 37:25–29 (1989).

Beri et al., "Biliverdin Reductase Activity in Relation to Bilirubin," *Biochemical Society Transactions* 20:353S (1992).

Kutty et al., "Rat Liver Cytochrome P–450b, P–420b, and P–420c are Degraded to Biliverdin by Heme Oxygenase," *Archives of Biochemistry and Biophysics* 260(2):638–644 (1988).

Bell et al., "Kinetic Properties and Regulation of Biliverdin Reductase," *Archives of Biochemistry and Biophysics* 263(1):1–9 (1988).

Kutty et al., "Hepatic Heme Metabolism: Possible Role of Biliverdin in the Regulation of Heme Oxygenase Activity," *Biochemical and Biophysical Research Communications* 122(1):40–46 (1984).

Yamaguchi et al., "Biliverdin–IXα Reductase and Biliverdin–IXβ Reductase from Human Liver," *J. Biol. Chem.* 269(3):24343–24348 (1994).

Maines, "New Developments in the Regulation of Heme Metabolism and Their Implications," *CRC Critical Reviews in Toxicology* 12(3):241–314 (1984).

Terry et al., "Inactivation of Phytochrome– and Phycobiliprotein–Chromophore Precursors by Rat Liver Biliverdin Reductase," *J. Biol. Chem.* 268(35):26099–26106 (1993).

Willis et al., "Heme Oxygenase: A Novel Target for the Modulation of the Inflammatory Response," *Nature Medicine* 2(1):87–90 (1996).

Maines, "Characterization of Heme Oxygenase Activity in Leydig and Sertoli Cells of the Rat Testes," *Biochemical Pharmacology* 33(9):1493–1502 (1984).

Lee et al., "Overexpression of Heme Oxygenase–1 in Human Pulmonary Epithelial Cells Results in Cell Growth Arrest and Increased Resistance to Hyperoxia," *Proc. Natl. Acad. Sci. USA* 93:10393–10398 (1996), pp. 10395–10397 missing.

Siow et al., "Heme Oxygenase–Carbon Monoxide Signalling Pathway in Atherosclerosis: Anti–Atherogenic Actions of Biliburin and Carbon Monoxide?," *Cardiovascular Research* 41:385–394 (1999).

Komuro et al., "Cloning and Characterization of the cDNA Encoding Human Biliverdin–IXα Reductase," *Biochimica et Biophysica Acta* 1309:89–99 (1996).

Cunningham et al., "Cloning, Overexpression and Purification of Biliverdin IXβ Reductase," *Biochemical Society Transactions* 25:S613 (1997).

Yamaguchi et al., "Complete Amino Acid Sequence of Biliverdin–IXβ Reductase from Human Liver," *Biochemical and Biophysical Research Communications* 197(3):1518–1523 (1993).

Ennis et al., "Expression of Rat Biliverdin Reductase as a Glutathione S–transferase Fusion Protein," *Biochemical Society Transactions* 23:443S (1995).

Bari et al., "The Interplay Between Basicity, Conformation, and Enzymatic Reduction in Biliverdins," *Biochemical and Biophysical Research Communications* 188(1):48–56 (1992).

Maines, "Multiple Forms of Biliverdin Reductase: Age–Related Change in Pattern of Expression in Rat Liver and Brain," *Molecular Pharmacology* 38:481–485 (1990).

Mayer et al., "Promotion of trans–Platinum In Vivo Effects on Renal Heme and Hemoprotein Metabolism by D, L–Buthionine–S,R–Sulfoximine," *Biochemical Pharmacology* 39(10):1565–1571 (1990).

Mancuso et al., "Activation of Heme Oxygenase and Consequent Carbon Monoxide Formation Inhibits the Release of Arginine Vasopressin from Rat Hypothalamic Explants. Molecular Linkage Between Heme Catabolism and Neuroendocrine Function," *Molecular Brain Research* 50:267–276 (1997).

Guerre et al., "Dose–Related Increase in Liver Heme Catabolism During Rabbit Aflatoxicosis," *Toxicology Letters* 92:101–108 (1997).

Ennis et al., "Cloning and Overexpression of Rat Kidney Biliverdin IXα Reductase as a Fusion Protein with Glutathione S–transferase: Stereochemistry of NADH Oxidation and Evidence that the Presence of the Glutathoine S–transferase Domain Does Not Effect BVR–A Activity," *Biochem J.* 326:33–36 (1997).

Lagarias et al., "Regulation of Photomorphogenesis by Expression of Mammalian Biliverdin Reductase in Transgenic Arabidopsis Plants," *The Plant Cell* 9:675–688 (1997).

Sagara et al., "Cellular Merchanisms of Resistance to Chronic Oxidative Stress," *Free Radical Biology & Medicine* 24(9):1375–1389 (1998).

Komuro et al., "Molecular Cloning and Expression of Human Liver Biliverdin–IXβ Reductase," *Biol. Pharm. Bull.* 19(6):796–804 (1996).

Maines et al., "The Oxidoreductase, Biliverdin Reductase is Induced in Human Renal Cacinoma—pH and Cofactor–Specific Increase in Activity," *J. Urology* 162:1467–1472 (1999).

* cited by examiner

SEQUENCE LISTING

<160> NUMBER OF SEQ ID NOS: 17

<210> SEQ ID NO 1
<211> LENGTH: 296
<212> TYPE: PRT
<213> ORGANISM: Homo sapiens

<400> SEQUENCE: 1

Met Asn Ala Glu Pro Glu Arg Lys Phe Gly Val Val Val Gly Val
 1               5                  10                  15

Gly Arg Ala Gly Ser Val Arg Met Arg Asp Leu Arg Asn Pro His Pro
                20                  25                  30

Ser Ser Ala Phe Leu Asn Leu Ile Gly Phe Val Ser Arg Arg Glu Leu
            35                  40                  45

Gly Ser Ile Asp Gly Val Gln Gln Ile Ser Leu Glu Asp Ala Leu Ser
        50                  55                  60

Ser Gln Glu Val Glu Val Ala Tyr Ile Cys Ser Glu Ser Ser His
 65                  70                  75                  80

Glu Asp Tyr Ile Arg Gln Phe Leu Asn Ala Gly Lys His Val Leu Val
                85                  90                  95

Glu Tyr Pro Met Thr Leu Ser Leu Ala Ala Ala Gln Glu Leu Trp Glu
            100                 105                 110

Leu Ala Glu Gln Lys Gly Lys Val Leu His Glu Glu His Val Glu Leu
        115                 120                 125

Leu Met Glu Glu Phe Ala Phe Leu Lys Lys Glu Val Val Gly Lys Asp
    130                 135                 140

Leu Leu Lys Gly Ser Leu Leu Phe Thr Ser Asp Pro Leu Glu Glu Asp
145                 150                 155                 160

Arg Phe Gly Phe Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
            180                 185                 190

Arg Lys Glu Asp Gln Tyr Met Lys Met Thr Val Cys Leu Glu Thr Glu
        195                 200                 205

Lys Lys Ser Pro Leu Ser Trp Ile Glu Glu Lys Gly Pro Gly Leu Lys
    210                 215                 220

Arg Asn Arg Tyr Leu Ser Phe His Phe Lys Ser Gly Ser Leu Glu Asn
225                 230                 235                 240

Val Pro Asn Val Gly Val Asn Lys Asn Ile Phe Leu Lys Asp Gln Asn
                245                 250                 255

Ile Phe Val Gln Lys Leu Leu Gly Gln Phe Ser Glu Lys Glu Leu Ala
            260                 265                 270

Ala Glu Lys Lys Arg Ile Leu His Cys Leu Gly Leu Ala Glu Glu Ile
        275                 280                 285

Gln Lys Tyr Cys Cys Ser Arg Lys
    290                 295

<210> SEQ ID NO 2
<211> LENGTH: 1070
<212> TYPE: DNA
<213> ORGANISM: Homo sapiens

<400> SEQUENCE: 2
ggggtggcgc ccggagctgc acggagagcg tgcccgtcag tgaccgaaga agagaccaag      60

-continued

```
atgaatgcag agcccgagag gaagtttggc gtggtggtgg ttggtgttgg ccgagccggc      120
tccgtgcgga tgagggactt gcggaatcca caccttcct cagcgttcct gaacctgatt      180
ggcttcgtgt cgagaaggga gctcgggagc attgatggag tccagcagat ttctttggag     240
gatgctcttt ccagccaaga ggtggaggtc gcctatatct gcagtgagag ctccagccat     300
gaggactaca tcaggcagtt ccttaatgct ggcaagcacg tccttgtgga atacccatg      360
acactgtcat tggcggccgc tcaggaactg tgggagctgg ctgagcagaa aggaaaagtc     420
ttgcacgagg agcatgttga actcttgatg gaggaattcg ctttcctgaa aaagaagtg      480
gtggggaaag acctgctgaa agggtcgctc ctcttcacat ctgacccgtt ggaagaagac     540
cggtttggct tccctgcatt cagcggcatc tctcgactga cctggctggt ctccctctttt    600
ggggagcttt ctcttgtgtc tgccactttg gaagagcgaa aggaagatca gtatatgaaa     660
atgacagtgt gtctggagac agagaagaaa agtccactgt catggattga agaaaaagga    720
cctggtctaa aacgaaacag atatttaagc ttccatttca gtctgggtc cttggagaat     780
gtgccaaatg taggagtgaa taagaacata tttctgaaag atcaaaatat atttgtccag    840
aaactcttgg gccagttctc tgagaaggaa ctggctgctg aaaagaaacg catcctgcac    900
tgcctggggc ttgcagaaga aatccagaaa tattgctgtt caaggaagta agaggaggag     960
gtgatgtagc acttccaaga tggcaccagc atttggttct tctcaagagt tgaccattat    1020
ctctattctt aaaattaaac atgttgggga acaaaaaaa aaaaaaaaa                  1070
```

<210> SEQ ID NO 3
<211> LENGTH: 296
<212> TYPE: PRT
<213> ORGANISM: Homo sapiens

<400> SEQUENCE: 3

```
Met Asn Thr Glu Pro Glu Arg Lys Phe Gly Val Val Val Gly Val
  1               5                  10                  15

Gly Arg Ala Gly Ser Val Arg Met Arg Asp Leu Arg Asn Pro His Pro
                 20                  25                  30

Ser Ser Ala Phe Leu Asn Leu Ile Gly Phe Val Ser Arg Arg Glu Leu
             35                  40                  45

Gly Ser Ile Asp Gly Val Gln Gln Ile Ser Leu Glu Asp Ala Leu Ser
         50                  55                  60

Ser Gln Glu Val Glu Val Ala Tyr Ile Cys Ser Glu Ser Ser His
 65                  70                  75                  80

Glu Asp Tyr Ile Arg Gln Phe Leu Asn Ala Gly Lys His Val Leu Val
                 85                  90                  95

Glu Tyr Pro Met Thr Leu Ser Leu Ala Ala Ala Gln Glu Leu Trp Glu
            100                 105                 110

Leu Ala Glu Gln Lys Gly Lys Val Leu His Glu Glu His Val Glu Leu
        115                 120                 125

Leu Met Glu Glu Phe Ala Phe Leu Lys Lys Glu Val Val Gly Lys Asp
    130                 135                 140

Leu Leu Lys Gly Ser Leu Leu Phe Thr Ala Gly Pro Leu Glu Glu Glu
145                 150                 155                 160

Arg Phe Gly Phe Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
            180                 185                 190

Arg Lys Glu Asp Gln Tyr Met Lys Met Thr Val Cys Leu Glu Thr Glu
```

```
                195                 200                 205
Lys Lys Ser Pro Leu Ser Trp Ile Glu Glu Lys Gly Pro Gly Leu Lys
            210                 215                 220

Arg Asn Arg Tyr Leu Ser Phe His Phe Lys Ser Gly Ser Leu Glu Asn
225                 230                 235                 240

Val Pro Asn Val Gly Val Asn Lys Asn Ile Phe Leu Lys Asp Gln Asn
                245                 250                 255

Ile Phe Val Gln Lys Leu Leu Gly Gln Phe Ser Glu Lys Glu Leu Ala
                260                 265                 270

Ala Glu Lys Lys Arg Ile Leu His Cys Leu Gly Leu Ala Glu Glu Ile
            275                 280                 285

Gln Lys Tyr Cys Cys Ser Arg Lys
            290                 295

<210> SEQ ID NO 4
<211> LENGTH: 295
<212> TYPE: PRT
<213> ORGANISM: Rattus norvegicus

<400> SEQUENCE: 4

Met Asp Ala Glu Pro Lys Arg Lys Phe Gly Val Val Val Gly Val
  1               5                  10                  15

Gly Arg Ala Gly Ser Val Arg Leu Arg Asp Leu Lys Asp Pro Arg Ser
                 20                  25                  30

Ala Ala Phe Leu Asn Leu Ile Gly Phe Val Ser Arg Arg Glu Leu Gly
             35                  40                  45

Ser Leu Asp Glu Val Arg Gln Ile Ser Leu Glu Asp Ala Leu Arg Ser
 50                  55                  60

Gln Glu Ile Asp Val Ala Tyr Ile Cys Ser Glu Ser Ser His Glu
 65                  70                  75                  80

Asp Tyr Ile Arg Gln Phe Leu Gln Ala Gly Lys His Val Leu Val Glu
                 85                  90                  95

Tyr Pro Met Thr Leu Ser Phe Ala Ala Ala Gln Glu Leu Trp Glu Leu
                100                 105                 110

Ala Ala Gln Lys Gly Arg Val Leu His Glu Glu His Val Glu Leu Leu
            115                 120                 125

Met Glu Glu Phe Glu Phe Leu Arg Arg Glu Val Leu Gly Lys Glu Leu
            130                 135                 140

Leu Lys Gly Ser Leu Arg Phe Thr Ala Ser Pro Leu Glu Glu Glu Arg
145                 150                 155                 160

Phe Gly Phe Pro Ala Phe Ser Gly Ile Ser Arg Leu Thr Trp Leu Val
                165                 170                 175

Ser Leu Phe Gly Glu Leu Ser Leu Ile Ser Ala Thr Leu Glu Glu Arg
                180                 185                 190

Lys Glu Asp Gln Tyr Met Lys Met Thr Val Gln Leu Glu Thr Gln Asn
            195                 200                 205

Lys Gly Leu Leu Ser Trp Ile Glu Glu Lys Gly Pro Gly Leu Lys Arg
            210                 215                 220

Asn Arg Tyr Val Asn Phe Gln Phe Thr Ser Gly Ser Leu Glu Glu Val
225                 230                 235                 240

Pro Ser Val Gly Val Asn Lys Asn Ile Phe Leu Lys Asp Gln Asp Ile
                245                 250                 255

Phe Val Gln Lys Leu Leu Asp Gln Val Ser Ala Glu Asp Leu Ala Ala
            260                 265                 270
```

```
Glu Lys Lys Arg Ile Met His Cys Leu Gly Leu Ala Ser Asp Ile Gln
    275                 280                 285
Lys Leu Cys His Gln Lys Lys
    290                 295

<210> SEQ ID NO 5
<211> LENGTH: 1081
<212> TYPE: DNA
<213> ORGANISM: Rattus norvegicus

<400> SEQUENCE: 5
ggtcaacagc taagtgaagc catatccata gagagtttgt gccagtgccc caagatcctg      60
aacctctgtc tgtcttcgga cactgactga agagaccgag atggatgccg agccaaagag     120
gaaatttgga gtggtagtgg ttggtgttgg cagagctggc tcggtgaggc tgagggactt     180
gaaggatcca cgctctgcag cattcctgaa cctgattgga tttgtgtcca gacgagagct     240
tgggagcctt gatgaagtac ggcagatttc tttggaagat gctctccgaa gccaagagat     300
tgatgtcgcc tatatttgca gtgagagttc cagccatgaa gactatatac ggcagtttct     360
gcaggctggc aagcatgtcc tcgtggaata ccccatgaca ctgtcatttg cggcggccca     420
ggagctgtgg gagctggccg cacagaaagg gagagtcctg catgaggagc acgtggaact     480
cttgatggag gaattcgaat tcctgagaag agaagtgttg gggaaagagc tactgaaagg     540
gtctcttcgc ttcacagcta gcccactgga agaagagaga tttggcttcc ctgcgttcag     600
cggcatttct cgcctgacct ggctggtctc cctcttcggg gagctttctc ttatttctgc     660
caccttggaa gagcgaaaag aggatcagta tatgaaaatg accgtgcagc tggagaccca     720
gaacaagggt ctgctgtcat ggattgaaga gaaagggcct ggcttaaaaa gaaacagata     780
tgtaaacttc cagttcactt ctgggtccct ggaggaagtg ccaagtgtag gggtcaataa     840
gaacattttc ctgaaagatc aggatatatt tgttcagaag ctcttagacc aggtctctgc     900
agaggacctg gctgctgaga agaagcgcat catgcattgc ctgggctgg ccagcgacat     960
ccagaagctt tgccaccaga agaagtgaag aggaagcttc agagacttct gaaggggcc    1020
agggtttggt cctatcaacc attcaccttt agctcttaca attaaacatg tcagataaac    1080
a                                                                    1081

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: hydrophobic
      domain of BVR
<221> NAME/KEY: PEPTIDE
<222> LOCATION: (2)
<223> OTHER INFORMATION: where X is any aa

<400> SEQUENCE: 6

Phe Xaa Val Val Val Val
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:  nucleotide
      binding domain of BVR
<221> NAME/KEY: PEPTIDE
<222> LOCATION: (2)
```

```
<223> OTHER INFORMATION: where X is any aa
<221> NAME/KEY: PEPTIDE
<222> LOCATION: (4)..(5)
<223> OTHER INFORMATION: where X is any aa

<400> SEQUENCE: 7

Gly Xaa Gly Xaa Xaa Gly
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:
      oxidoreductase domain of BVR

<400> SEQUENCE: 8

Ala Gly Leu His Val Leu Val Glu
 1               5

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence:  leucine
      zipper of BVR
<221> NAME/KEY: PEPTIDE
<222> LOCATION: (2)..(7)
<223> OTHER INFORMATION: where X is any aa
<221> NAME/KEY: PEPTIDE
<222> LOCATION: (9)..(14)
<223> OTHER INFORMATION: where X is any aa
<221> NAME/KEY: PEPTIDE
<222> LOCATION: (16)..(21)
<223> OTHER INFORMATION: where X is any aa
<221> NAME/KEY: PEPTIDE
<222> LOCATION: (23)..(28)
<223> OTHER INFORMATION: where X is any aa

<400> SEQUENCE: 9

Leu Xaa Xaa Xaa Xaa Xaa Xaa Leu Xaa Xaa Xaa Xaa Xaa Xaa Lys Xaa
 1               5                  10                  15

Xaa Xaa Xaa Xaa Xaa Leu Xaa Xaa Xaa Xaa Xaa Xaa Leu
            20                  25

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: kinase
      motif of BVR

<400> SEQUENCE: 10

Ser Arg Arg
 1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:  kinase
      motif of BVR
```

```
<400> SEQUENCE: 11

Lys Gly Ser
 1

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence:  kinase
      motif of BVR
<221> NAME/KEY: PEPTIDE
<222> LOCATION: (3)
<223> OTHER INFORMATION: where X is any aa

<400> SEQUENCE: 12

Phe Thr Xaa
 1

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:  nuclear
      localization signal of BVR

<400> SEQUENCE: 13

Gly Leu Lys Arg Asn Arg Tyr
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: methylation
      site of BVR

<400> SEQUENCE: 14

Pro Gly Leu Lys Arg
 1               5

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: zinc finger
      domain of BVR
<221> NAME/KEY: PEPTIDE
<222> LOCATION: (3)..(12)
<223> OTHER INFORMATION: where X is any aa

<400> SEQUENCE: 15

His Cys Xaa Xaa Xaa Xaa Xaa Xaa Xaa Xaa Xaa Xaa Cys Cys
 1               5                  10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:  protein
      kinase C enhancing domain
<221> NAME/KEY: PEPTIDE
<222> LOCATION: (5)
<223> OTHER INFORMATION: where X is any aa
```

```
<400> SEQUENCE: 16

Lys Lys Arg Ile Xaa His Cys
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:  protein
      kinase C inhibiting domain
<221> NAME/KEY: PEPTIDE
<222> LOCATION: (3)
<223> OTHER INFORMATION: where X is any aa
<221> NAME/KEY: PEPTIDE
<222> LOCATION: (5)..(7)
<223> OTHER INFORMATION: where X is any aa

<400> SEQUENCE: 17

Gln Lys Xaa Cys Xaa Xaa Xaa Lys
 1               5
```

METHODS OF MODIFYING CELL STRUCTURE AND REMODELING TISSUE

This application claims the benefit of U.S. Provisional Patent Application Ser. No. 60/261,500, filed Jan. 12, 2001, which is hereby incorporated by reference in its entirety.

This work was supported by the U.S. National Institutes of Health under Grant Nos. ES04066 and ES04391. The U.S. Government may have certain rights in the invention.

FIELD OF THE INVENTION

The present invention relates to methods of modifying cell structure and remodeling tissue which involve modulating the intracellular levels of biliverdin reductase or active fragments or variants thereof.

BACKGROUND OF THE INVENTION

Biliverdin reductase ("BVR") catalyzes reduction of the γ-meso bridge of biliverdin, an open tetrapyrrole, to produce bilirubin (Singleton et al., *J. Biol. Chem.* 240: 47890–4789 (1965); Tenhunen et al., *Biochemistry* 9:298–303 (1970); Colleran et al., *Biochem J.* 119:16P–19P (1970); Kutty et al., *J. Biol. Chem.* 256:3956–3962 (1981); Buldain et al., *Eur. J. Biochem.* 156:179–184 (1986); Noguchi et al., *Biochem J.* 86:833–839 (1989)). In mammals, the oxidative cleavage of heme is catalyzed by the heme oxygenase system (Maines, *Ann. Rev. Pharmacol. Toxicol.* 37:517–554 (1997)). Because open tetrapyrroles are generally believed to be devoid of biological functions, the enzymes that catalyze their formation have not traditionally been in the main stream of research activity. In plants, however, biliverdin analogues, phytochromobilins, function in photoregulatory capacity (Terry et al., *J. Biol. Chem.* 266:22215–22221 (1991); Cornejo et al., *J. Biol. Chem.* 267:14790–14798 (1992)). Molecular cloning and biochemical analyses have shown that the enzyme, which in human is a 296 residue polypeptide, is highly conserved both at its primary structure and at its unique catalytic properties (Fakhrai et al., *J. Biol. Chem.* 267:4023–4029 (1992); McCoubrey et al., *Eur. J Biochem.* 222:597–603 (1994); McCoubrey et al., *Gene* 160:235–240 (1995); Maines et al., *Eur. J. Biochem.* 235:372–381 (1996)). BVR is the only enzyme described to date with dual pH/dual adenine nucleotide cofactor requirements (Kutty et al., *J. Biol. Chem.* 256:3956–3962 (1981); Fakhrai et al., *J. Biol. Chem.* 267:4023–4029 (1992); Maines et al., *Eur. J. Biochem.* 235:372–381 (1996); Huang et al., *J. Biol. Chem.* 264:7844–7849 (1989)). The reductase uses NADH in the acidic range (optimum range ~pH 6.0–6.7), whereas NADPH is utilized in the basic range (optimum range ~pH 8.5–8.7). BVR, which is a zinc metalloprotein (Maines et al., *Eur. J. Biochem.* 235:372–381 (1996)), possesses a $HCX_{10}CH$ or $HCX_{10}CC$ motif in the carboxy terminal third of the protein, which is similar to the zinc binding motif of protein kinase C (Hubbard et al., *Science* 254:1776–1779 (1991)) and may be the site of interaction of BVR with zinc.

BVR was previously thought to be simply a housekeeping enzyme found in most mammalian cells in excess of, or in disproportionate levels to, heme oxygenase isozymes (Ewing et al., *J. Neurochem.* 61:1015–1023 (1993)). Yet it has the above-noted noted unique and uncommon properties. Examination of the primary structure of human BVR, which recently became available (Maines et al., *Eur. J. Biochem.* 235:372–381 (1996)), revealed the presence of consensus sequences that are conserved in protein kinases, the most notable one being the GXGXXG motif near the N terminus of the protein that is found invariably in all kinases (Kamps et al., *Nature* 310:589–592 (1984); Hunter et al., *Ann. Rev. Biochem.* 54:897–930 (1985); Schlessinger, *Trend. Biochem. Sci.* 13:443–447 (1988); Hanks et al., *Science* 241:42–52 (1988); Yarden et al., *Annu. Rev. Biochem.* 57:443–478 (1988); Hanks et al., *Methods Enzymol.* 200:38–62 (1991)). A valine residue is present in BVR just 2 positions downstream from the last glycine of this motif. A valine residue is invariant at the corresponding position, as in BVR, in the family of kinases that phosphorylate G-protein coupled receptors (Garcia-Bustos et al., *Biochim. Biophys. ACTA* 1071:83–101 (1991)). Database search results also identified additional similarities with PKGs, including a cluster of charged residues (KRNR) in the carboxy terminus of BVR. Such clusters are a characteristic of the nuclear localization signal ("NLS") (Garcia-Bustos et al., *Biochim. Biophys. ACTA* 1071:83–101 (1991)).

Although BVR has previously been identified as exhibiting protective effects against oxidative stress and as sharing characteristics with known kinases (see U.S. patent application Ser. No. 09/606,129 to Maines, filed Jun. 28, 2000), it is unclear the extent to which BVR is implicated in cellular repair mechanisms. The present invention is directed to overcoming the above-identified deficiencies in the art.

SUMMARY OF THE INVENTION

A first aspect of the present invention relates to a method of modifying cell structure which includes: increasing the intracellular concentration of biliverdin reductase, or a fragment or variant thereof, in a mammalian cell under conditions effective to modify the structure of the mammalian cell.

A second aspect of the present invention relates to a method of in vivo tissue remodeling in a mammal which includes: delivering biliverdin reductase, or fragments or variants thereof, to one or more cells present at a site of tissue remodeling in a mammal, wherein said delivering increases the intracellular concentration of biliverdin reductase, or fragments or variants thereof, under conditions effective to modify the structure of the one or more cells at the site of tissue remodeling, thereby remodeling the tissue containing the one or more cells.

A third aspect of the present invention relates to a method of repairing a damaged organ or organ system by performing the in vivo tissue modeling of the present invention, where the site of tissue remodeling is within the damaged organ or organ system.

DETAILED DESCRIPTION OF THE INVENTION

Figure 1:
FIGS. 1–6 show different images of HeLa cells transfected with human BVR DNA. Differences between untransfected cells (normal morphology) and transfected cells (immunostained) is readily apparent. The transfected cells show remarkable enlargement, altered cellular morphology including filopodia, and the appearance of spikes which are clearly observed.

The methods of modifying cell structure and remodeling tissue according to the present invention involve modulating the intracellular levels of biliverdin reductase ("BVR") or active fragments thereof. Modulating intracellular levels of BVR can be achieved using known recombinant techniques directed to cells or tissues to be affected, as described below, or by using known protein delivery techniques for delivering BVR into cells or tissues to be affected.

One form of human biliverdin reductase ("hBVR") has an amino acid sequence corresponding to SEQ. ID. No. 1 as follows:

| | | | | | | | | | | | | | | |
|---|---|---|---|---|---|---|---|---|---|---|---|---|---|---|
| Met | Asn | Ala | Glu | Pro | Glu | Arg | Lys | Phe | Gly | Val | Val | Val | Gly | Val |
| 1 | | | | 5 | | | | | 10 | | | | | 15 |
| Gly | Arg | Ala | Gly | Ser | Val | Arg | Met | Arg | Asp | Leu | Arg | Asn | Pro | His | Pro |
| | | | 20 | | | | | 25 | | | | | 30 | | |
| Ser | Ser | Ala | Phe | Leu | Asn | Leu | Ile | Gly | Phe | Val | Ser | Arg | Arg | Glu | Leu |
| | | 35 | | | | | 40 | | | | | 45 | | | |
| Gly | Ser | Ile | Asp | Gly | Val | Gln | Gln | Ile | Ser | Leu | Glu | Asp | Ala | Leu | Ser |
| | 50 | | | | | 55 | | | | | 60 | | | | |
| Ser | Gln | Glu | Val | Glu | Val | Ala | Tyr | Ile | Cys | Ser | Glu | Ser | Ser | Ser | His |
| 65 | | | | | 70 | | | | | 75 | | | | | 80 |
| Glu | Asp | Tyr | Ile | Arg | Gln | Phe | Leu | Asn | Ala | Gly | Lys | His | Val | Leu | Val |
| | | | | 85 | | | | | 90 | | | | | 95 | |
| Glu | Tyr | Pro | Met | Thr | Leu | Ser | Leu | Ala | Ala | Ala | Gln | Glu | Leu | Trp | Glu |
| | | | 100 | | | | | 105 | | | | | 110 | | |
| Leu | Ala | Glu | Gln | Lys | Gly | Lys | Val | Leu | His | Glu | Glu | His | Val | Glu | Leu |
| | | 115 | | | | | 120 | | | | | 125 | | | |
| Leu | Met | Glu | Glu | Phe | Ala | Phe | Leu | Lys | Lys | Glu | Val | Val | Gly | Lys | Asp |
| | 130 | | | | | 135 | | | | | 140 | | | | |
| Leu | Leu | Lys | Gly | Ser | Leu | Leu | Phe | Thr | Ser | Asp | Pro | Leu | Glu | Glu | Asp |
| 145 | | | | | 150 | | | | | 155 | | | | | 160 |
| Arg | Phe | Gly | Phe | Pro | Ala | Phe | Ser | Gly | Ile | Ser | Arg | Leu | Thr | Trp | Leu |
| | | | | 165 | | | | | 170 | | | | | 175 | |
| Val | Ser | Leu | Phe | Gly | Glu | Leu | Ser | Leu | Val | Ser | Ala | Thr | Leu | Glu | Glu |
| | | | | 180 | | | | | 185 | | | | | 190 | |
| Arg | Lys | Glu | Asp | Gln | Tyr | Met | Lys | Met | Thr | Val | Cys | Leu | Glu | Thr | Glu |
| | | | 195 | | | | | 200 | | | | | 205 | | |
| Lys | Lys | Ser | Pro | Leu | Ser | Trp | Ile | Glu | Glu | Lys | Gly | Pro | Gly | Leu | Lys |
| | | 210 | | | | | 215 | | | | | 220 | | | |
| Arg | Asn | Arg | Tyr | Leu | Ser | Phe | His | Phe | Lys | Ser | Gly | Ser | Leu | Glu | Asn |
| 225 | | | | | 230 | | | | | 235 | | | | | 240 |
| Val | Pro | Asn | Val | Gly | Val | Asn | Lys | Asn | Ile | Phe | Leu | Lys | Asp | Gln | Asn |
| | | | | 245 | | | | | 250 | | | | | 255 | |
| Ile | Phe | Val | Gln | Lys | Leu | Leu | Gly | Gln | Phe | Ser | Glu | Lys | Glu | Leu | Ala |
| | | | 260 | | | | | 265 | | | | | 270 | | |
| Ala | Glu | Lys | Lys | Arg | Ile | Leu | His | Cys | Leu | Gly | Leu | Ala | Glu | Glu | Ile |
| | | 275 | | | | | 280 | | | | | 285 | | | |
| Gln | Lys | Tyr | Cys | Cys | Ser | Arg | Lys |
| | 290 | | | | | 295 | |

Heterologous expression and isolation of hBVR is described in Maines et al., *Eur. J. Biochem.* 235(1–2):372–381 (1996); Maines et al., *Arch. Biochem. Biophys.* 300(1):320–326 (1993), each of which is hereby incorporated by reference in its entirety. The DNA molecule encoding this form of hBVR has a nucleotide sequence corresponding to SEQ. ID. No. 2 as follows:

```
ggggtggcgc ccggagctgc acggagagcg tgcccgtcag tgaccgaaga agagaccaag    60
atgaatgcag agcccgagag gaagtttggc gtggtggtgg ttggtgttgg ccgagccggc   120
tccgtgcgga tgagggactt gcggaatcca caccttcct cagcgttcct gaacctgatt   180
ggcttcgtgt cgagaaggga gctcgggagc attgatggag tccagcagat ttctttggag   240
gatgctcttt ccagccaaga ggtggaggtc gcctatatct gcagtgagag ctccagccat   300
```

-continued

```
gaggactaca tcaggcagtt ccttaatgct ggcaagcacg tccttgtgga atacccatg    360 acactgtcat tggcggccgc tcaggaactg tgggagctgg ctgagcagaa aggaaaagtc   420
ttgcacgagg agcatgttga actcttgatg gaggaattcg ctttcctgaa aaagaagtg    480 gtggggaaag acctgctgaa aggtcgctc ctcttcacat ctgacccgtt ggaagaagac   540
cggtttggct ccctgcatt cagcggcatc tctcgactga cctggctggt ctccctcttt   600
ggggagcttt ctcttgtgtc tgccactttg gaagagcgaa aggaagatca gtatatgaaa   660
atgacagtgt gtctggagac agagaagaaa agtccactgt catggattga agaaaaagga   720
cctggtctaa aacgaaacag atatttaagc ttccatttca gtctgggtc cttggagaat   780 gtgccaaatg taggagtgaa taagaacata tttctgaaag atcaaaatat atttgtccag   840
aaactcttgg gccagttctc tgagaaggaa ctggctgctg aaaagaaacg catcctgcac   900
tgcctggggc ttgcagaaga atccagaaa tattgctgtt caaggaagta agaggaggag   960
gtgatgtagc acttccaaga tggcaccagc atttggttct tctcaagagt tgaccattat  1020
ctctattctt aaaattaaac atgttgggga aacaaaaaaa aaaaaaaaa             1070
```

The open reading frame which encodes hBVR of SEQ. ID. No. 1 extends from nt 1 to nt 888.

Another form of hBVR has an amino acid sequence according to SEQ. ID. No. 3 as follows:

```
Met Asn Thr Glu Pro Glu Arg Lys Phe Gly Val Val Val Gly Val
 1               5                  10                  15

Gly Arg Ala Gly Ser Val Arg Met Arg Asp Leu Arg Asn Pro His Pro
                20                  25                  30

Ser Ser Ala Phe Leu Asn Leu Ile Gly Phe Val Ser Arg Arg Glu Leu
                35                  40                  45

Gly Ser Ile Asp Gly Val Gln Gln Ile Ser Leu Glu Asp Ala Leu Ser
            50                  55                  60

Ser Gln Glu Val Glu Val Ala Tyr Ile Cys Ser Glu Ser Ser His
65                  70                  75                  80

Glu Asp Tyr Ile Arg Gln Phe Leu Asn Ala Gly Lys His Val Leu Val
                85                  90                  95

Glu Tyr Pro Met Thr Leu Ser Leu Ala Ala Ala Gln Glu Leu Trp Glu
                100                 105                 110

Leu Ala Glu Gln Lys Gly Lys Val Leu His Glu Glu His Val Glu Leu
                115                 120                 125

Leu Met Glu Glu Phe Ala Phe Leu Lys Lys Glu Val Val Gly Lys Asp
            130                 135                 140

Leu Leu Lys Gly Ser Leu Leu Phe Thr Ala Gly Pro Leu Glu Glu Glu
145                 150                 155                 160

Arg Phe Gly Phe Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
                180                 185                 190

Arg Lys Glu Asp Gln Tyr Met Lys Met Thr Val Cys Leu Glu Thr Glu
                195                 200                 205

Lys Lys Ser Pro Leu Ser Trp Ile Glu Glu Lys Gly Pro Gly Leu Lys
            210                 215                 220

Arg Asn Arg Tyr Leu Ser Phe His Phe Lys Ser Gly Ser Leu Glu Asn
225                 230                 235                 240

Val Pro Asn Val Gly Val Asn Lys Asn Ile Phe Leu Lys Asp Gln Asn
                245                 250                 255
```

-continued

```
Ile Phe Val Gln Lys Leu Leu Gly Gln Phe Ser Glu Lys Glu Leu Ala
            260                 265                 270

Ala Glu Lys Lys Arg Ile Leu His Cys Leu Gly Leu Ala Glu Glu Ile
        275                 280                 285

Gln Lys Tyr Cys Cys Ser Arg Lys
    290                 295
```

This hBVR sequence is reported at Komuro et al., NCBI Accession No. G02066, direct submission to the EMBL Data Library (1998), which is hereby incorporated by reference in its entirety. Differences between the hBVR of SEQ. ID. No. 1 and the hBVR of SEQ. ID. No. 3 are at aa residues 3, 154, 155, and 160. Thus, residue 3 can be either alanine or threonine, residue 154 can be either alanine or serine, residue 155 can be either aspartic acid or glycine, and residue 160 can be either aspartic acid or glutamic acid.

One form of rat biliverdin reductase ("rBVR") has an amino acid sequence corresponding to SEQ. ID. No. 4 as follows:

```
Met Asp Ala Glu Pro Lys Arg Lys Phe Gly Val Val Val Gly Val
 1               5                  10                  15

Gly Arg Ala Gly Ser Val Arg Leu Arg Asp Leu Lys Asp Pro Arg Ser
            20                  25                  30

Ala Ala Phe Leu Asn Leu Ile Gly Phe Val Ser Arg Arg Glu Leu Gly
        35                  40                  45

Ser Leu Asp Glu Val Arg Gln Ile Ser Leu Glu Asp Ala Leu Arg Ser
    50                  55                  60

Gln Glu Ile Asp Val Ala Tyr Ile Cys Ser Glu Ser Ser Ser His Glu
65                  70                  75                  80

Asp Tyr Ile Arg Gln Phe Leu Gln Ala Gly Lys His Val Leu Val Glu
                85                  90                  95

Tyr Pro Met Thr Leu Ser Phe Ala Ala Ala Gln Glu Leu Trp Glu Leu
            100                 105                 110

Ala Ala Gln Lys Gly Arg Val Leu His Glu Glu His Val Glu Leu Leu
        115                 120                 125

Met Glu Glu Phe Glu Phe Leu Arg Arg Glu Val Leu Gly Lys Glu Leu
    130                 135                 140

Leu Lys Gly Ser Leu Arg Phe Thr Ala Ser Pro Leu Glu Glu Glu Arg
145                 150                 155                 160

Phe Gly Phe Pro Ala Phe Ser Gly Ile Ser Arg Leu Thr Trp Leu Val
                165                 170                 175

Ser Leu Phe Gly Glu Leu Ser Leu Ile Ser Ala Thr Leu Glu Glu Arg
            180                 185                 190

Lys Glu Asp Gln Tyr Met Lys Met Thr Val Gln Leu Glu Thr Gln Asn
        195                 200                 205

Lys Gly Leu Leu Ser Trp Ile Glu Glu Lys Gly Pro Gly Leu Lys Arg
    210                 215                 220

Asn Arg Tyr Val Asn Phe Gln Phe Thr Ser Gly Ser Leu Glu Glu Val
225                 230                 235                 240

Pro Ser Val Gly Val Asn Lys Asn Ile Phe Leu Lys Asp Gln Asp Ile
                245                 250                 255

Phe Val Gln Lys Leu Leu Asp Gln Val Ser Ala Glu Asp Leu Ala Ala
            260                 265                 270

Glu Lys Lys Arg Ile Met His Cys Leu Gly Leu Ala Ser Asp Ile Gln
        275                 280                 285

Lys Leu Cys His Gln Lys Lys
    290                 295
```

Heterologous expression and isolation of rBVR is described in Fakhrai et al., *J. Biol. Chem.* 267(6):4023–4029 (1992), which is hereby incorporated by reference in its entirety. The rBVR of SEQ. ID. No. 4 shares about 82% aa identity to the hBVR of SEQ. ID. No. 1, with variations in aa residues being highly conserved. The DNA molecule encoding this form of rBVR has a nucleotide sequence corresponding to SEQ. ID. No. 5 as follows:

```
ggtcaacagc taagtgaagc catatccata gagagtttgt gccagtgccc caagatcctg    60
aacctctgtc tgtcttcgga cactgactga agagaccgag atggatgccg agccaaagag   120
gaaatttgga gtggtagtgg ttggtgttgg cagagctggc tcggtgaggc tgagggactt   180
gaaggatcca cgctctgcag cattcctgaa cctgattgga tttgtgtcca gacgagagct   240
tgggagcctt gatgaagtac ggcagatttc tttggaagat gctctccgaa gccaagagat   300
tgatgtcgcc tatatttgca gtgagagttc cagccatgaa gactatatac ggcagtttct   360
gcaggctggc aagcatgtcc tcgtggaata ccccatgaca ctgtcatttg cggcggccca   420
ggagctgtgg gagctggccg cacagaaagg gagagtcctg catgaggagc acgtggaact   480
cttgatggag gaattcgaat tcctgagaag agaagtgttg gggaaagagc tactgaaagg   540
gtctcttcgc ttcacagcta gcccactgga agaagagaga tttggcttcc ctgcgttcag   600
cggcatttct cgcctgacct ggctggtctc cctcttcggg gagctttctc ttatttctgc   660
caccttggaa gagcgaaaag aggatcagta tatgaaaatg accgtgcagc tggagaccca   720
gaacaagggt ctgctgtcat ggattgaaga gaaagggcct ggcttaaaaa gaaacagata   780
tgtaaacttc cagttcactt ctgggtccct ggaggaagtg ccaagtgtag gggtcaataa   840
gaacattttc ctgaaagatc aggatatatt tgttcagaag ctcttagacc aggtctctgc   900
agaggacctg gctgctgaga agaagcgcat catgcattgc ctggggctgg ccagcgacat   960
ccagaagctt tgccaccaga agaagtgaag aggaagcttc agagacttct gaaggggcc   1020 agggtttggt cctatcaacc attcaccttt agctcttaca attaaacatg tcagataaac   1080
a                                                                    1081
```

The open reading frame which encodes rBVR of SEQ. ID. No. 4 extends from nt 1 to nt 885.

By way of example, hBVR of SEQ. ID. No. 1 characterized by a number of functional domains, including putative and/or demonstrated phosphorylation sites from aa 15 to 20, aa 21 to 23, aa 44 to 46 or 47, aa 49 to 54, aa 58 to 61, aa 64 to 67, aa 78, to 81, aa 79 to 82, aa 189 to 192, aa 207 to 209, aa 214 to 217, aa 222 to 227, aa 236 to 241, aa 245 to 250, aa 267 to 269 or 270, and aa 294 to 296; a basic N-terminal domain characterized by aa 6 to 8; a hydrophobic domain characterized by aa 9 to 14 (FXVVVV, SEQ. ID. No. 6); a nucleotide binding domain characterized by aa 15 to 20 (GXGXXG, SEQ. ID. No. 7); an oxidoreductase domain characterized by aa 90 to 97 (AGKHVLVE, SEQ. ID. No. 8); a leucine zipper spanning aa 129 to 157 ($LX_6LX_6KX_6LX_6L$, SEQ. ID. No. 9); several kinase motifs, including aa 44 to 46 (SRR, SEQ. ID. No. 10), aa 147 to 149 (KGS, SEQ. ID. No. 11) and aa 162 to 164 (FGX, SEQ. ID. No. 12); a nuclear localization signal spanning aa 222 to 228 (GLKRNRY, SEQ. ID. No. 13); a myristylation site spanning aa 221 to 225 (PGLKR, SEQ. ID. No. 14); a zinc finger domain spanning aa 280 to 293 ($HCX_{10}CC$, SEQ. ID. No. 15); and substrate binding domains including, without limitation, a protein kinase C ("PKC") enhancing domain spanning aa 275 to 281 (KKRIXHC, SEQ. ID. No. 16) and a PKC inhibiting domain spanning aa 289 to 296 (QKXCXXXK, SEQ. ID. No. 17). By way of sequence comparison and, in consideration of conserved substitutions, hBVR of SEQ. ID. No. 3 and rBVR of SEQ. ID. No.4 include similar functional domains. For example rBVR includes an identical hydrophobic domain, an identical nucleotide binding domain, an identical oxidoreductase domain, a conserved leucine zipper domain (with residue variations between L and K residues), identical or conserved kinase motifs, an identical nuclear localization signal, an identical myristylation site, a conserved zinc finger domain (with terminal C residue replaced by H), a conserved PKC enhancing domain, and a conserved PKC inhibiting domain.

DNA molecules encoding a BVR protein or polypeptide can also include a DNA molecule that hybridizes under stringent conditions to the DNA molecule having a nucleotide sequence of SEQ. ID. No. 2 or SEQ. ID. No. 5. An example of suitable stringency conditions is when hybridization is carried out at a temperature of about 37° C. using a hybridization medium that includes 0.9M sodium citrate ("SSC") buffer, followed by washing with 0.2×SSC buffer at 37° C. Higher stringency can readily be attained by increasing the temperature for either hybridization or washing conditions or increasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 42° C. to about 65° C. for up to about 20 hours in a hybridization medium containing 1M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 µg/ml *E. coli* DNA, followed by washing carried out at between about 42° C. to about 65° C. in a 0.2×SSC buffer.

The BVR protein or polypeptide can also be a fragment of the above biliverdin reductase proteins or polypeptides or a variant thereof.

Fragments of BVR preferably contain one or more of the above-listed functional domains, and possess one or more of the activities of full length BVR. Suitable fragments can be produced by several means. Subclones of a gene encoding a known BVR can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity, e.g., converting biliverdin to bilirubin, modifying cell structure, etc., as discussed infra. See also Huang et al., *J. Biol. Chem.* 264:7844–7849 (1989), which is hereby incorporated by reference in its entirety.

In another approach, based on knowledge of the primary structure of the protein, fragments of a BVR gene may be synthesized using the PCR technique together with specific sets of primers chosen to represent particular portions of the protein. Erlich et al., *Science* 252:1643–51 (1991), which is hereby incorporated by reference in its entirety. These can then be cloned into an appropriate vector for expression of a truncated protein or polypeptide from bacterial cells as described above. For example, oligomers of at least about 15 to 20 nt in length can be selected from the nucleic acid molecules of SEQ. ID. No. 2 and SEQ ID. No. 5 for use as primers.

In addition, chemical synthesis can also be employed using techniques well known in the chemistry of proteins such as solid phase synthesis (Merrifield, *J. Am. Chem. Assoc.* 85:2149–2154 (1964), which is hereby incorporated by reference in its entirety) or synthesis in homogenous solution (Houbenweyl, *Methods of Organic Chemistry*, ed. E. Wansch, Vol. 15, I and II, Thieme, Stuttgart (1987), which is hereby incorporated by reference in its entirety).

Variants of suitable BVR proteins or polypeptides can also be expressed. Variants may be made by, for example, the deletion, addition, or alteration of amino acids that have either (i) minimal influence on certain properties, secondary structure, and hydropathic nature of the polypeptide or (ii) substantial effect on one or more properties of BVR. Variants of BVR can also be fragments of BVR which include one or more deletion, addition, or alteration of amino acids of the type described above. The BVR variant preferably contains a deletion, addition, or alteration of amino acids within one of the above-listed functional domains. The substituted or additional amino acids can be either L-amino acids, D-amino acids, or modified amino acids, preferably L-amino acids. Whether a substitution, addition, or deletion results in modification of BVR variant activity may depend, at least in part, on whether the altered amino acid is conserved. Conserved amino acids can be grouped either by molecular weight or charge and/or polarity of R groups, acidity, basicity, and presence of phenyl groups, as is known in the art.

A number of BVR variants have been described in co-pending U.S. patent application Ser. No. 09/606,129 to Maines, filed Jun. 28, 2000, which is hereby incorporated by reference in its entirety.

Variants may also include, for example, a polypeptide conjugated to a signal (or leader) sequence at the N-terminal end of the protein which co-translationally or post-translationally directs transfer of the protein. The polypeptide may also be conjugated to a linker or other sequence for ease of synthesis, purification, identification, or therapeutic use (i.e., delivery) of the polypeptide.

The BVR protein or polypeptide can be recombinantly produced, isolated, and then purified, if necessary. When recombinantly produced, the biliverdin reductase protein or polypeptide is expressed in a recombinant host cell, typically, although not exclusively, a prokaryote.

When a prokaryotic host cell is selected for subsequent transformation, the promoter region used to construct the recombinant DNA molecule (i.e., transgene) should be appropriate for the particular host. The DNA sequences of eukaryotic promoters, as described infra for expression in eukaryotic host cells, differ from those of prokaryotic promoters. Eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgamo ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. Coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Mammalian cells can also be used to recombinantly produce BVR or fragments or variants thereof.

Suitable mammalian host cells include, without limitation: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, and NS-1 cells. Suitable expression vectors for directing expression in mammalian cells generally include a promoter, as well as other transcription and translation control sequences known in the art. Common promoters include, without limitation, SV40, MMTV, metallothionein-1, adenovirus Ela, CMV, immediate early, immunoglobulin heavy chain promoter and enhancer, and RSV-LTR.

Regardless of the selection of host cell, once the DNA molecule coding for a biliverdin reductase protein or polypeptide, or fragment or variant thereof, has been ligated to its appropriate regulatory regions using well known molecular cloning techniques, it can then be introduced into a suitable vector or otherwise introduced directly into a host cell using transformation protocols well known in the art (Sambrook et al., *Molecular Cloning: A Laboratory Manual*, Second Edition, Cold Spring Harbor Press, NY (1989), which is hereby incorporated by reference in its entirety).

The recombinant molecule can be introduced into host cells via transformation, particularly transduction, conjugation, mobilization, or electroporation. Suitable host cells include, but are not limited to, bacteria, virus, yeast, mammalian cells, insect, plant, and the like. The host cells, when grown in an appropriate medium, are capable of expressing the biliverdin reductase, or fragment or variant thereof, which can then be isolated therefrom and, if necessary, purified. The BVR, or fragment or variant thereof, is preferably produced in purified form (preferably at least about 60%, more preferably 80%, pure) by conventional techniques.

For therapeutic purposes, the treated cell is preferably in vivo and the protein or polypeptide or RNA molecule is delivered into the cell in a manner which affords the protein or polypeptide or RNA molecule to be active within the cell. A number of known delivery techniques can be utilized for the delivery, into cells, of either proteins or polypeptides or RNA, or DNA molecules encoding them.

Regardless of the particular method of the present invention which is practiced, when it is desirable to contact a cell (i.e., to be treated) with a protein or polypeptide or RNA molecule, it is preferred that the contacting be carried out by delivery of the protein or polypeptide or RNA molecule into the cell.

One approach for delivering protein or polypeptides or RNA molecules into cells involves the use of liposomes. Basically, this involves providing a liposome which includes that protein or polypeptide or RNA to be delivered, and then contacting the target cell with the liposome under conditions effective for delivery of the protein or polypeptide or RNA into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. USA* 84:7851 (1987); *Biochemistry* 28:908 (1989), which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., *J. Mol. Biol.* 13:238–252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

An alternative approach for delivery of proteins or polypeptides involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptides involves preparation of chimeric proteins according to U.S. Pat. No. 5,817,789 to Heartlein et al., which is hereby incorporated by reference in its entirety. The chimeric protein can include a ligand domain and, e.g., BVR or a fragment or variant thereof. The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein.

When it is desirable to achieve heterologous expression of a desirable protein or polypeptide or RNA molecule in a target cell, DNA molecules encoding the desired protein or polypeptide or RNA can be delivered into the cell. Basically, this includes providing a nucleic acid molecule encoding the protein or polypeptide and then introducing the nucleic acid molecule into the cell under conditions effective to express the protein or polypeptide or RNA in the cell. Preferably, this is achieved by inserting the nucleic acid molecule into an expression vector before it is introduced into the cell.

When transforming mammalian cells for heterologous expression of a protein or polypeptide, an adenovirus vector can be employed. Adenovirus gene delivery vehicles can be readily prepared and utilized given the disclosure provided in Berkner, *Biotechniques* 6:616–627 (1988) and Rosenfeld et al., *Science* 252:431–434 (1991), WO 93/07283, WO 93/06223, and WO 93/07282, each of which is hereby incorporated by reference in its entirety. Adeno-associated viral gene delivery vehicles can be constructed and used to deliver a gene to cells. The use of adeno-associated viral gene delivery vehicles in vitro is described in Chatterjee et al., *Science* 258:1485–1488 (1992); Walsh et al., *Proc. Nat'l. Acad. Sci.* 89:7257–7261 (1992); Walsh et al., *J. Clin Invest.* 94:1440–1448 (1994); Flotte et al., *J. Biol. Chem.* 268:3781–3790 (1993); Ponnazhagan et al., *J. Exp. Med.* 179:733–738 (1994); Miller et al., *Proc. Nat'l Acad. Sci.* 91:10183–10187 (1994); Einerhand et al., *Gene Ther.* 2:336–343 (1995); Luo et al., *Exp. Hematol.* 23:1261–1267 (1995); and Zhou et al., *Gene Ther.* 3:223–229 (1996), each of which is hereby incorporated by reference in its entirety. In vivo use of these vehicles is described in Flotte et al., *Proc. Nat'l Acad. Sci.* 90:10613–10617 (1993); and Kaplitt et al., *Nature Genet.* 8:148–153 (1994), each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; and U.S. Pat. No. 5,885,808 to Spooner et al.; and U.S. Pat. No. 5,871,727 to Curiel, each of which is hereby incorporated by reference in its entirety.

Retroviral vectors which have been modified to form infective transformation systems can also be used to deliver nucleic acid encoding a desired protein or polypeptide or RNA product into a target cell. One such type of retroviral vector is disclosed in U.S. Pat. No. 5,849,586 to Kriegler et al., which is hereby incorporated by reference in its entirety.

Regardless of the type of infective transformation system employed, it can be targeted for delivery of the nucleic acid to a specific cell type. For example, for delivery of the nucleic acid into specific cells, a high titer of the infective transformation system can be injected directly within the desired site so as to enhance the likelihood of cell infection within the desired site. The infected cells will then express the desired protein product, in this case BVR, or fragments or variants thereof, to modify the structure of those cells which have been infected.

Whether the proteins or polypeptides or nucleic acids are administered alone or in combination with pharmaceutically or physiologically acceptable carriers, excipients, or stabilizers, or in solid or liquid form such as, tablets, capsules, powders, solutions, suspensions, or emulsions, they can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. For most therapeutic purposes, the proteins or polypeptides or nucleic acids can be administered intravenously.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the proteins or polypeptides or nucleic acids in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Both the biliverdin reductase and fragments or variants thereof can be delivered to the target cells (i.e., at or around the site where cell modification is desired) using the above-described methods for delivering such therapeutic products. In delivering the therapeutic products to nerve cells in the brain, consideration should be provided to negotiation of the blood-brain barrier. The blood-brain barrier typically prevents many compounds in the blood stream from entering the tissues and fluids of the brain. Nature provides this mechanism to insure a toxin-free environment for neurologic function. However, it also prevents delivery to the brain of compounds, in this case neuroprotective compounds that can inhibit nerve cell death following an ischemic event.

One approach for negotiating the blood-brain barrier is described in U.S. Pat. No. 5,752,515 to Jolesz et al., which is hereby incorporated by reference in its entirety. Basically, the blood-brain barrier is temporarily "opened" by targeting a selected location in the brain and applying ultrasound to induce, in the central nervous system (CNS) tissues and/or fluids at that location, a change detectable by imaging. A protein or polypeptide or RNA molecule of the present invention can be delivered to the targeted region of the brain while the blood-brain barrier remains "open," allowing targeted neuronal cells to uptake the delivered protein or polypeptide or RNA. At least a portion of the brain in the vicinity of the selected location can be imaged, e.g., via magnetic resonance imaging, to confirm the location of the change. Alternative approaches for negotiating the blood-brain barrier include chimeric peptides and modified liposome structures which contain a PEG moiety (reviewed in Pardridge, *J. Neurochem.* 70:1781–1792 (1998), which is hereby incorporated by reference in its entirety), as well as osmotic opening (i.e., with bradykinin, mannitol, RPM7, etc.) and direct intracerebral infusion (Kroll et al., *Neurosurgery* 42(5):1083–1100 (1998), which is hereby incorporated by reference in its entirety).

Analysis of the promoter region associated with the nucleic acid encoding rBVR indicates the presence of recognition sites for several regulating proteins, including INF-1, an enhancer of cytokine and virus-induced transcriptional activation, and AP-1, the proto-oncogene binding site (McCoubrey et al., "The Structure, Organization and Differential Expression of the Rat Gene Encoding Biliverdin Reductase," Gene 160:235–240 (1995), which is hereby incorporated by reference in its entirety. Also, two elements known to be involved in embryonic gene expression, P3A and engrailed, are present in the promoter region of this gene. These criteria are consistent with the function of BVR in a regulatory capacity in the cell.

As discussed in greater detail in the Examples, it has been discovered that transformation of mammalian cells with biliverdin reductase is effective in modifying the structure of the transformed mammalian cells. It is believed that the increase in biliverdin reductase in the cell is responsible for having modified cell structure. Therefore, one aspect of the present invention relates to a method of modifying cell structure which includes: increasing the intracellular concentration of biliverdin reductase, or a fragment or variant thereof, in a mammalian cell under conditions effective to modify the structure of the mammalian cell.

Where the cellular concentration of biliverdin reductase is increased, it should be appreciate that some basal level of biliverdin reductase may exist in the cell which has been targeted. Thus, the increase in biliverdin reductase intracellular concentration is simply the result of causing more biliverdin reductase to be expressed (e.g., inducing or transforming) or introducing additional biliverdin reductase from an external source (i.e., administration).

In contrast, because biliverdin reductase fragments and variants are not normally expressed in mammalian cells, any increase in biliverdin reductase fragments or variants is the result of their heterologous expression (i.e., transforming) or introducing biliverdin reductase fragments or variants from an external source (i.e., administering).

Regardless of whether it is biliverdin reductase or its fragments or variants whose cellular concentration is increased in the mammalian cell to be modified, the increase in concentration can be achieved by introducing the BVR or BVR fragments or variants into the cell. Typically, this is done by contacting the mammalian cell (to be modified) with a delivery vehicle which includes biliverdin reductase or a fragment or variant thereof. The delivery vehicle can be any delivery vehicle of the type described above for protein delivery.

Likewise, such increase in cellular concentration can be achieved by heterologous expression by the mammalian cell (to be modified). Such heterologous expression is typically the result of transforming the mammalian cell with a nucleic acid encoding biliverdin reductase or a fragment or variant thereof under conditions effective for expression of the biliverdin reductase or the fragment or variant thereof in the mammalian cell. The transformation can be achieved using any nucleic acid delivery system of the type described above. (e.g., infective transformation).

The mammalian cells which can be treated include, without limitation, stem cells (both omnipotent and pluripotent stem cells), neuronal or glial cells, vascular smooth muscle cells, skeletal muscle cells, epithelial cells, and nucleated blood cells (e.g., macrophages and other blood cells). The mammalian cells whose structure is modified can be either in vitro or in vivo when their structure is modified.

Exemplary aspects of the mammalian cell structure which can be modified in accordance with the present invention include, without limitation, enhanced cell size (i.e., forming giant cells), actin microspike formation, polar cell morphology (i.e., with protracted filopodia extensions), and a combination thereof.

Without being bound by theory, it is believed that the modified cell structure is the result of biliverdin reductase interaction with proteins and kinases that govern cell cycling and with polypeptide growth factors.

In view of the modified cell structure, it is further contemplated that the present invention can be utilized to perform organogenesis, tissue remodeling, wound healing, angiogenesis, or combinations thereof. Tissue remodeling, of course, encompasses both wound healing and angiogenesis.

Thus, a further aspect of the present invention relates to a method of performing in vivo tissue remodeling in a mammal. This aspect of the invention includes: delivering biliverdin reductase, or fragments or variants thereof, to one or more cells present at a site of tissue remodeling in a mammal, wherein the delivering (of BVR or its fragments or variants) increases the intracellular concentration of biliverdin reductase, or fragments or variants thereof, under conditions effective to modify the structure of the one or more cells at the site of tissue remodeling, thereby remodeling the tissue containing the one or more cells.

Tissues which can be remodeled in vivo include, without limitation, epithelial tissues, nerve tissues, muscular tissues (both smooth muscle and skeletal muscle tissues), or connective tissue. More specifically, angiogenesis can implicate remodeling of vascular tissue and modifying the structure of vascular smooth muscle, bladder, and urinary tract cells. Likewise, wound healing can implicate remodeling of epithelial tissues, nerve tissues, muscular tissues (both smooth muscle and skeletal muscle tissues), or connective tissues via modifying the structures of epithelial cells, nerve or glial cells, vascular and skeletal muscle cells, etc.

As a result of such tissue remodeling, where multiple tissues are remodeled, it also contemplated to utilize the present invention according to a method of repairing a damaged organ or organ system by performing the method of in vivo tissue remodeling in accordance with the present invention, where the site of tissue remodeling is within the damaged organ or organ system. Exemplary organ or organ systems which can be subject to repair include, without limitation, skin, liver, nervous system (e.g., both sensory neurons and motor neurons), cardiovascular system, and urogenital tract.

With respect specifically to wound healing, it should be appreciated that the primary goal in the treatment of wounds is to achieve wound closure. Open cutaneous wounds represent one major category of wounds and include burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age (see Hunt and Goodson, 1988). In general, agents which promote a more rapid influx of fibroblasts, endothelial and epithelial cells into wounds should increase the rate at which wounds heal. By virtue of increasing the intracellular concentration of biliverdin reductase, it becomes possible to induce an increase in cell size, the formation of actin microspikes, and morphological changes in cell polarity, i.e., formation of filopodia extensions. These aspects suggest that the affected cells can be made more readily able to influx into damage sites in need of repair.

The use of BVR for wound healing can also be carried out in combination with a medicament selected from the group consisting of an antibacterial agent, an antiviral agent, an antifungal agent, an antiparasitic agent, an anti-inflammatory agent, an analgesic agent, an antipruritic agent, or a combination thereof. For cutaneous wound healing, a preferred mode of administration is by the topical route.

EXAMPLES

The following examples are intended to illustrate, but by no means are intended to limit, the scope of the present invention as set forth in the appended claims.

Example 1

In Vitro Transformation of HeLa Cells with Biliverdin Reductase for Modifying Cellular Structure HeLa cells were transfected in vitro with biliverdin reductase encoding DNA. A HeLa cell suspension having a density of about $12 \times 10^4$/ml was introduced to a 12-well plate using 0.2 ml of the cell suspension per well (i.e., about $2.4 \times 10^4$ cells per well). The following protocol was employed for transfection:

Cells were washed with DMEM(serum). Thereafter, the following solution was added: 2 μl of DNA (541 0.5 μg/μl), 50 μl of DMEM(-), and 2 μl of lipofectimine. After 4–5 h, 0.5 ml of DMEM (20% serum) was added followed by 30 h incubation (37° C.).

On the following day cells were immunostained using the following protocol. HeLa cells were washed once for 5 min PBS (0.1% PB, 0.9% NaCl), followed by treatment with 4% PFA (on ice). 10 min later, cells were washed 3 times for 5 min each time in PBS. Cells were blocked by treatment with PBS (950 μl)+50 μl horse serum (5% HS PBS) for 1 h at room temperature. Cells were treated with a solution of 3% HS—0.25% Triton-PBS at 4° C. overnight, thereafter cells were treated with 1:1000 dilution of BVR antibody.

For antibody staining, cells were washed 3 times for 5 min each time in PBS—0.25% Triton×100 and treated with second antibody solution consisting of: horse serum, 15 μl/ml and antimouse-IgG, 5 μl/ml. After 3 times washing with PBS for 5 min each time, cells were visualized using ABC solution (Vector Labs) and stained for 30 min.

Figure 2:
Figure 3:
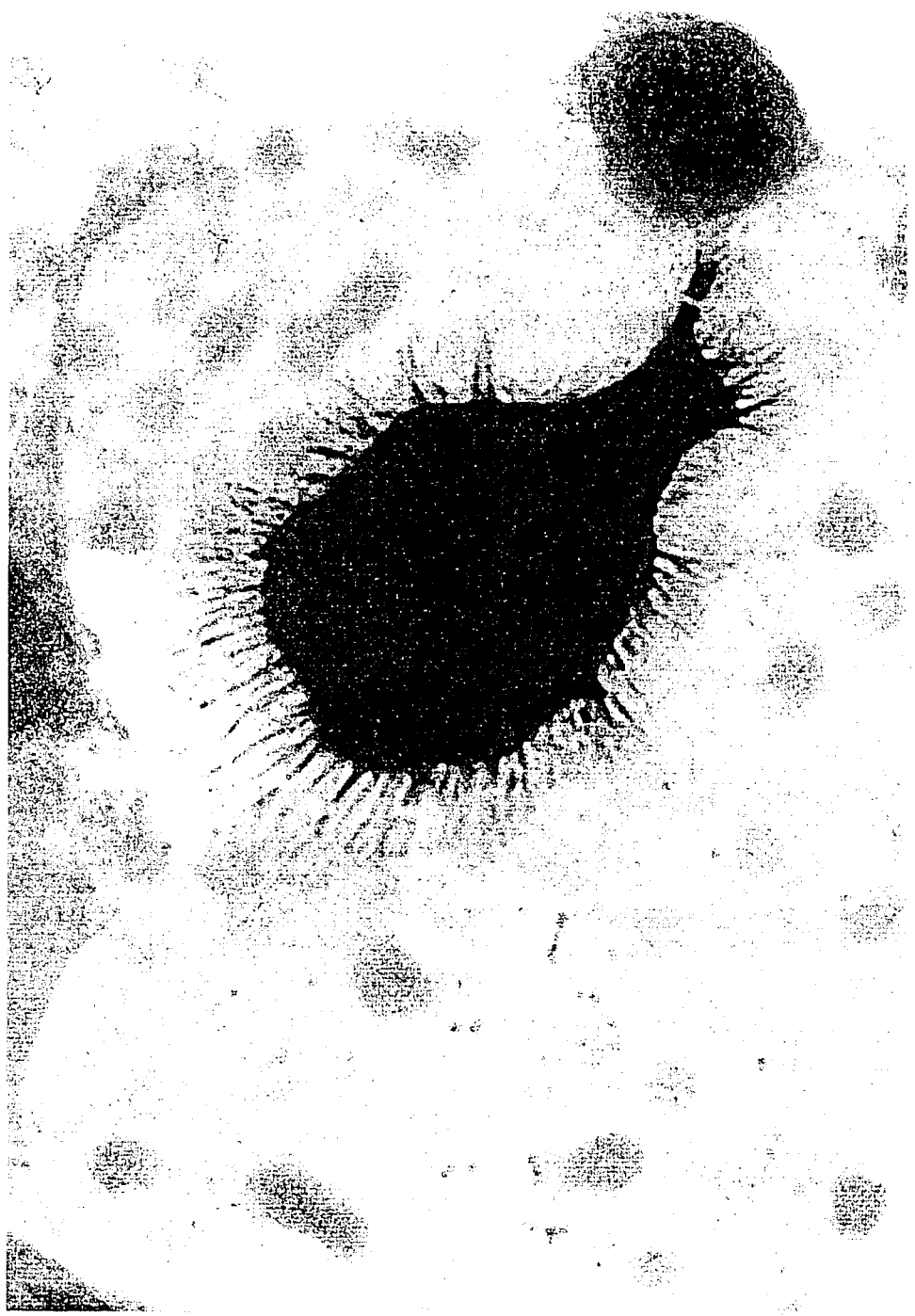
Figure 4:
Figure 5:
Figure 6:

Non specific staining was removed using 3% of $H_2O_2$. Cells were then washed with dd $H_2O$ and dehydrated in 95%–100% ethanol, xylene 5 min. Slides were mounted with ½ permount+½ xylene Control and transformed HeLa cells were visualized by immunostaining using antibody to BVR. As shown in FIGS. 1–6, the transformed HeLa cells displayed larger cell size relative to control cells, formation of actin microspikes, and polar cell morphology with filopodia extensions.

The above results indicate that BVR is a regulator of cell proliferation and cell differentiation. Following transformation to induce an increase in BVR expression, transfected cells were transformed into giant cells several times the size of normal cells. Moreover, the transfected cells displayed formation of actin microspikes. Such actin microspikes are known to act as sensory devices by which cells explore their environment. Also, BVR transfected cells exhibited polar cell morphology, as characterized by protracted filopodia extensions that resemble that of neuronal axon and dendritic extensions, a phenotype which is not displayed by Cdc42 transfected cells (Adams and Schwarz, "Stimulation of Fasein Spikes by Thrombospondin-1 is Mediated by GTPases Rac and Cdc42," *J. Cell Biol.* 150:807–822 (2000), which is hereby incorporated by reference in its entirety). These properties are displayed by certain cyclin-dependent kinases. Specifically, Cdc42 kinase stimulates spike formation (Kozma et al., "The Ras-related protein Cdc42Hs and Bradykinin Promote Formation of Peripheral Actin Microspikes and Filopodia in Swiss 3T3 Fibroblasts," *Mol. Cell Biol.* 15:1942–1952 (1995); Nobes and Hall, "Rho, Rac, and Cdc42 GTPases Regulate the Assembly of Multimolecular Focal Complexes Associated with Actin Stress Fibers, Lamellipodia, and Filopodia," *Cell* 81:53–62 (1995); Adams and Schwarz, "Stimulation of Fasein Spikes by Thrombospondin-1 is Mediated by GTPases Rac and Cdc42, "*J. Cell Biol.* 150:807–822 (2000), each of which is hereby incorporated by reference in its entirety) and D type cyclins, e.g., cyclin $D_2$, deregulate cell size and cause cell mass increase (Kershoff and Ziff, "Cyclin $D_2$ Ha-Ras Transformed Rat Embryo Fibroblasts Exhibit Novel Deregulation of Cell Size Control and Early S Phase Arrest in Low Serum," *EMBO J.* 14:1892–1903 (1995), which is hereby incorporated by reference in its entirety). These proteins require cooperation of signal transduction kinase activity, e.g., GTPases Rac/Ha-Ras (Adams and Schwarz, "Stimulation of Fasein Spikes by Thrombospondin-1 is Mediated by GTPases Rac and Cdc42," *J. Cell Biol.* 150:807–822 (2000); Kershoff and Ziff, "Cyclin $D_2$ and Ha-Ras Transformed Rat Embryo Fibroblasts Exhibit Novel Deregulation of Cell Size Control and Early S Phase Arrest in Low Serum," *EMBO J.* 14:1892–1903 (1995), each of which is hereby incorporated by reference in its entirety). BVR, as noted above, is a protein kinase and has both cell proliferating and cell differentiation activities. Furthermore, BVR can unexpectedly control the cell size under normal conditions, whereas cyclin $D_2$ and Ha-Ras transformed cells only display giant size in low serum conditions. The morphology of the above-described transformed cells is also consistent with the use of BVR expression for promoting axonal growth in the case of nerve damage.

In a number of amino acid sequences, X is used to depict a residue which can be any naturally occurring amino acid, unless otherwise indicated.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of modifying cell structure comprising:

introducing into a mammalian cell a nucleic acid molecule encoding biliverdin reductase under conditions effective to express biliverdin reductase, thereby increasing the intracellular concentration of biliverdin reductase and modifying the structure of the mammalian cell, wherein the biliverdin reductase is encoded by a nucleic acid molecule that hybridizes to the complement of SEQ ID NO: 2 under hybridization conditions comprising a temperature of 65° C. and a hybridization medium comprising 1 M Na+ buffer and remains hybridized following wash conditions comprising a temperature of 65° C. and a wash medium comprising 0.2×SSC buffer, and wherein the modified cell structure is enhanced cell size, actin microspike formation, polar cell morphology, or a combination thereof.

2. The method according to claim 1 wherein said introducing comprises:

transfecting the mammalian cell with an infective transformation vector comprising the nucleic acid encoding biliverdin reductase.

3. The method according to claim 2 wherein the infective transformation vector is an adenovirus vector or a retrovirus vector.

4. The method according to claim 1 wherein the mammalian cell is a stem cell, a neuronal or glial cell, a vascular smooth muscle cell, a skeletal muscle cell, an epithelial cell, or a nucleated blood cell.

5. The method according to claim 1 wherein the mammalian cell is in vitro.

* * * * *

UNITED STATES PATENT AND TRADEMARK OFFICE
CERTIFICATE OF CORRECTION

PATENT NO. : 6,969,610 B2  
APPLICATION NO. : 10/045545  
DATED : November 29, 2005  
INVENTOR(S) : Mahin D. Maines It is certified that error appears in the above-identified patent and that said Letters Patent is hereby corrected as shown below:

At Col. 1, lines 7-9, delete:
"This work was supported by the U.S. National Institutes of Health under Grant Nos. ES04066 and ES04391. The U.S. Government may have certain rights in the invention.";
and insert in its place:
--This invention was made with government support under grants ES04066 and ES04391 awarded by National Institutes of Health. The government has certain rights in the invention.--.

Signed and Sealed this

Nineteenth Day of May, 2009

JOHN DOLL  
*Acting Director of the United States Patent and Trademark Office*